United States Patent [19]

Giselbrecht et al.

[11] Patent Number: 5,874,637
[45] Date of Patent: Feb. 23, 1999

[54] PROCESS FOR THE PURIFICATION OF O-PHTHALALDEHYDE

[75] Inventors: Karl Heinz Giselbrecht, Pasching; Klaus Reiter, Linz; Eduard Perndorfer, Traun; Rudolf Hermanseder, Pennewang, all of Austria

[73] Assignee: DSM Chemie Linz GmbH, Austria

[21] Appl. No.: 960,618

[22] Filed: Oct. 29, 1997

[30] Foreign Application Priority Data

Oct. 30, 1996 [AT] Austria ................................. A 1890/96

[51] Int. Cl.$^6$ ..................................................... C07C 45/27
[52] U.S. Cl. ............................................ 568/430; 568/425
[58] Field of Search ..................................... 568/430, 425

[56] References Cited

U.S. PATENT DOCUMENTS 4,769,464  9/1988  Sajtos .
5,326,438  7/1994  Hermeling .

FOREIGN PATENT DOCUMENTS 44 07 986  9/1994  Germany .

OTHER PUBLICATIONS

Sturrock et al. Canadian Journal of Chemistry, 49, pp. 3047–3051, 1971.

*Primary Examiner*—Gary Geist
*Assistant Examiner*—Sreeni Padmanabhan

[57] ABSTRACT

Process for the purification of o-phthalaldehyde in which an alcoholic solution containing the crude, unpurified o-phthalaldehyde is adjusted to a pH between 0 and 3 at a temperature between 0° and 60° C., then an alkaline solution is added, and the corresponding dialkoxyphthalan is extracted from the organic phase and purified by distillation and, when required, converted into the purified o-phthalaldehyde by hydrolysis.

9 Claims, No Drawings

PROCESS FOR THE PURIFICATION OF O-PHTHALALDEHYDE

Phthalaldehydes are used in many fields, for example as intermediates in the preparation of dyes, optical brighteners or special polymers. For this reason, several preparation variants have already been described. For example, o-phthalaldehyde (OPA) can be obtained, for example according to AT 380,008, by ozonolysis of naphthalene with subsequent extraction. The disadvantage of this process is that the ester which forms as a by-product can be removed from the OPA only with difficulty and to an inadequate degree. In addition, OPA is a reactive compound which is thermally and oxidatively unstable.

In order to screen the aldehyde from unintentional reactions, EP-A1-0 522 312 describes the possibility of using o-phthalaldehyde tetraalkyl acetals as depot compounds. These depot compounds are prepared according to EP-A1-0 522 312 by electrochemical oxidation. However, phthalaldehyde tetraalkyl acetals bind a relatively large amount of alcohol, as a result of which a large storage volume is required.

The object of the present invention was to find a process which permits the preparation of high-purity o-phthalaldehyde via a depot compound which binds less alcohol and thus requires a smaller storage volume and a shorter saponification time and which has a lower boiling point.

Surprisingly, this object has been achieved by a process in which OPA is prepared via a purification step with dialkoxyphthalan as intermediate.

Accordingly, the present invention relates to a process for the purification of o-phthalaldehyde which comprises adjusting an alcoholic solution containing the crude, unpurified o-phthalaldehyde to a pH between 0 and 3 at a temperature between 0° and 60° C., then adding an alkaline solution, and extracting the corresponding dialkoxyphthalan from the organic phase and purifying it by distillation, and, when required, converting it into the pure o-phthalaldehyde by hydrolysis.

To carry out the process according to the invention, a solution of an OPA, obtained by any desired preparation process, in an alcohol having 1 to 4 carbon atoms is firstly prepared. Alcohols having 1 to 4 carbon atoms are methanol, ethanol, propanol and butanol. Preference is given to methanol and ethanol, and particular preference to methanol.

The OPA to be purified can, for example, be prepared from dimethoxybenzene, by an electrochemical route or by ozonolysis of naphthalene. Preference is given to an OPA prepared by ozonolysis, for example according to Austrian Patent 380,008. If an OPA prepared by ozonolysis of naphthalene is used as starting material, it is already in the form of an alcoholic solution after ozonolysis, reduction of the peroxides and subsequent removal of the catalyst. In addition to the unpurified OPA, this solution also contains naphthalene, phthalide, methoxy-phthalan, and aldehydic acids and aldehydic esters, such as glyoxal, glycolates or glyoxylates, or fragments thereof or their sodium salts, the degree of impurity depending on the quality of the hydrogenation catalyst and being between 5 and 90%. The purification process according to the invention is independent of the nature and the content of impurities.

The alcoholic solution containing the unpurified OPA is then adjusted to a pH between 0 and 3, preferably between 0.5 and 2, by acidification. Suitable acidifiers are mineral acids, such as HCl, $H_2SO_4$, $H_3PO_4$, organic acids, such as formic acid, acetic acid, p-toluenesulfonic acid or methylsulfonic acid, or acidic ion exchangers. Preference is given to mineral acids, and particular preference to $H_2SO_4$. The temperature in this step is from 0° to 60° C., preferably from 15° to 30° C. Acidification converts the OPA to be purified into the corresponding dialkoxyphthalan.

Any sodium sulfate precipitate that forms is removed and the remaining solution of the phthalan formed is mixed with up to 50% aqueous alkaline solution in the next step. Examples of suitable alkaline solutions are sodium hydroxide solution and potassium hydroxide solution. Preference is given to sodium hydroxide solution.

The alcohol used as solvent is subsequently or simultaneously distilled off. The chosen pressure and temperature depend on the alcohol used. Distilling off the alcohol leaves a salt solution containing the phthalan. If solid salts are present in this solution, it is diluted with water in order to dissolve these salts.

Whilst the impurities such as esters, acids etc. remain in the aqueous phase as sodium salts, the corresponding dialkoxyphthalan is extracted from the organic phase using common extractants, such as, for example, ethers, for example diethyl ether, diisopropyl ether, methyl tert-butyl ether etc., or using ethyl acetate or toluene etc.

Preferred extractants are methyl tert-butyl ether, ethyl acetate and toluene. The chosen temperature during the extraction process is dependent on the extractant used and is preferably between room temperature and 80° C. The resultant dialkoxyphthalan can be purified by distillation, after which it is in the form of a colorless liquid which can be stored indefinitely at room temperature.

In order to obtain the OPA again, the dialkoxyphthalan is saponified either immediately or when required. This is carried out in the usual way by hydrolysis at a pH between 0 and 7, preferably between 0 and 3, using mineral acids, such as HCl, $H_2SO_4$, $H_3PO_4$, or organic acids, such as acetic acid, formic acid and p-toluenesulfonic acid or methanesulfonic acid.

The reaction temperature depends on the alkoxy radical of the phthalan and is preferably between room temperature and 100° C. The eliminated alcohol and, if necessary, the acid are then distilled off under reduced pressure. If necessary, the OPA can also be recrystallized, for example from diisopropyl ether, ethyl acetate, toluene, methyl tert-butyl ether or diethyl ether. The process according to the invention can provide high-purity (up to above 99.7, determined by GC) OPA which contains no oxidized by-products and thus has a longer shelf life than an OPA obtained by a process known from the prior art.

EXAMPLE 1

The starting solution was a methanolic hydrogenation solution from the ozonolysis plant of DSM Chemie Linz, obtained by ozonolysis of naphthalene. Following removal of the catalyst, the solution contained the following compounds

|  | (Area % GC) |
|---|---|
| Naphthalene | 16.2 |
| Methoxyphthalan | 8.3 |
| o-Phthalaldehyde (OPA) | 69.0 |
| Dimethoxyphthalan | 1.3 |
| Phthalate | 3.9 |
| Acetal ester | 0.4 |
| OPA tetramethyl acetal | 1.0 |

4000 ml of hydrogenation solution of the above composition having a pH of 6.05 were adjusted to pH 1.35 using 7 ml of conc. $H_2SO_4$. The sodium sulfate precipitate (21.8 g) was then filtered off, and 150 g of 20% strength sodium hydroxide solution were added to the filtrate, which contained the acetylated OPA. To remove the eliminated alcohol, the resultant solution was evaporated at 50° C. and 150 mbar, leaving 306 g of residue. The residue was then extracted with 60 g of water and 160 g of toluene and again with 250 g of toluene. The combined toluene phases were then evaporated on a rotary evaporator at 50° C. and 20 mbar. Yield of crude dimethoxyphthalan: 129.1 g
Aqueous phase: Yield: 261 g

EXAMPLE 2

4000 ml of hydrogenation solution (pH 6.08) were adjusted to a pH of 1.32 as in Example 1 using 7 ml of conc. $H_2SO_4$ and stirred overnight. After the precipitate had been filtered off, 150 g of 40% strength NaOH were added to the filtrate and the mixture was then evaporated on a rotary evaporator to remove the eliminated alcohol. 200 ml of water and 200 ml of toluene were added to the remaining bottom product, and the dimethoxyphthalan was extracted. For this, the intermediate phase which formed was firstly filtered off and the toluene phase was evaporated at 50° C. and 20 mbar. Yield: 109.9 g of crude dimethoxyphthalan

EXAMPLE 3

The yields of dimethoxyphthalan from Examples 1 and 2 were combined and worked up together.
Total quantity of dimethoxyphthalan: 239.0 g.
Work-up was effected by fractional vacuum distillation:

| Fraction | Oil bath T(°C.) | Still temp. (°C.) | Head temp. (°C.) | RR To:Rx | Vacuum (mbar) | Final weight (g) |
|---|---|---|---|---|---|---|
| 1 | 20–97 | 26–88 | up to 22.8 | 1:2 | 13 | 9.9 |
| 2 | * | | | | 13 | 7.2 |
| 3 | ** | 125 | 102 | | 13 | 8.2 |
| 4 | 160 | 125 | 84–109.5 | 1:2 | 13 | 8.2 |
| 5 | 160 | 125 | 109.5–111.6 | 1:2 | 13 | 18.7 |
| 6 | 160–170 | 125–141 | 111.6–117.6 | To | 13 | 124.1 |
| Bottom product | | | | | | 29.0 |

RR: Reflux ratio
To: Take-off
Rx: Reflux
*: Distillation head blocked by naphthalene
Distillation interrupted and cleaned.
**: After restarting, the head blocked again.
The solid dissolved when heated.

300 ml of acetic acid/water mixture (1:1) were added to fraction 6, and the mixture was evaporated on a rotary evaporator at 50° C. and 100–20 mbar. Yield: 125 g. 300 ml of acetone were then added to the remaining bottom product, which was again evaporated. Yield: 123 g. Since complete deacetalation had still not been achieved, a further 200 ml of acetic acid/water mixture (1:1) were added to the residue, which was again evaporated at 50° C. and 20 mbar. Yield: 123 g.

This step was repeated using 200 ml of acetic acid/water mixture at 100 mbar and 60° C. Yield: 98 g.

Since approximately 5% of acetal was still present, a further 100 ml of acetic acid/water mixture had to be added and the mixture evaporated at 60° C. and 100 mbar. Yield of OPA: 95.8 g.

The resultant OPA was then recrystallized from 300 ml of diisopropyl ether (DIPE) with the addition of 1 g of active carbon, and placed in a refrigerator at 40C. The solid formed was then filtered off with suction and washed with 50 ml of cold DIPE.
Yield of OPA: 75.1 g.
Purity: 99.96 (area %, GC).

We claim:

1. A process for the purification of o-phthalaldehyde which comprises adjusting an alcoholic solution containing the crude, unpurified o-phthalaldehyde to a pH between 0 and 3 at a temperature between 0° and 600° C., then adding an alkaline solution, and extracting the corresponding dialkoxyphthalan from the organic phase and purifying it by distillation, and, when required, converting it into the purified o-phthalaldehyde by hydrolysis.

2. The process as claimed in claim 1, wherein the crude, unpurified o-phthalaldehyde is dissolved in an alcohol having 1 to 4 carbon atoms.

3. The process as claimed in claim 1, wherein the alcoholic solution is adjusted to a pH between 0 and 3by addition of a mineral acid, an organic acid or an acidic ion exchanger.

4. The process as claimed in claim 3, wherein the mineral acid used is HCl, $H_2SO_4$ or $H_3PO_4$, and the organic acid used is formic acid, acetic acid, p-toluenesulfonic acid or methanesulfonic acid.

5. The process as claimed in claim 1, wherein the alkaline solution used is sodium hydroxide solution or potassium hydroxide solution.

6. The process as claimed in claim 1, wherein the hydrolysis is carried out at a pH of from 0 to 3 using a mineral acid or organic acid.

7. The process as claimed in claim 1, wherein the dialkoxyphthalan is extracted from the organic phase using diethyl ether, diisopropyl ether, methyl tert-butyl ether, ethyl acetate or toluene.

8. The process as claimed in claim 1, wherein a crude o-phthalaldehyde obtained by any desired preparation process is used as the starting material.

9. The process as claimed in claim 1, wherein a solution obtained by ozonolysis of naphthalene in methanol with subsequent reduction of the resultant peroxides and removal of the hydrogenation catalyst is used as the alcoholic solution containing crude, unpurified o-phthalaldehyde.

* * * * *